United States Patent [19]

Olsson et al.

[11] Patent Number: 5,519,543
[45] Date of Patent: May 21, 1996

[54] OPTIC SYSTEM FOR A DOWN HOLE CAMERA ASSEMBLY

[75] Inventors: Mark S. Olsson, San Diego, Calif.; Michael S. DiMascio, Windermere, Fla.

[73] Assignee: Hitwell Video, Inc., Lexington, Ky.

[21] Appl. No.: 94,163

[22] PCT Filed: Jan. 31, 1992

[86] PCT No.: PCT/US92/00874

§ 371 Date: Oct. 4, 1993

§ 102(e) Date: Oct. 4, 1993

[87] PCT Pub. No.: WO92/14034

PCT Pub. Date: Aug. 20, 1992

Related U.S. Application Data

[63] Continuation-in-part of Ser. No. 648,551, Jan. 31, 1991, abandoned.

[51] Int. Cl.⁶ .................................................. G02B 5/00
[52] U.S. Cl. ........................................... 359/894; 359/503
[58] Field of Search ..................... 385/100, 115, 385/117; 359/503, 821, 895, 820, 894

[56] References Cited

U.S. PATENT DOCUMENTS

| 221,713 | 11/1879 | Allen . | |
| 4,432,286 | 2/1984 | Witte | 110/193 |
| 4,629,888 | 12/1986 | Wolk | 250/256 |
| 4,649,274 | 3/1987 | Hartmann | 250/341.5 |
| 4,855,820 | 8/1989 | Barbour | 348/85 |
| 4,965,601 | 10/1990 | Canty | 354/63 |
| 5,123,723 | 6/1992 | Chesnutt | 359/503 |
| 5,124,838 | 6/1992 | Forkey et al. | 359/821 |

FOREIGN PATENT DOCUMENTS

| 1220632 | 7/1966 | Germany . |
| 2247139 | 4/1973 | Germany . |
| 1097585 | 1/1968 | United Kingdom . |

*Primary Examiner*—Georgia Y. Epps
*Assistant Examiner*—Thomas Robbins
*Attorney, Agent, or Firm*—King & Schickli

[57] ABSTRACT

An optic system is provided for a down hole camera. The system includes an elongated tubular housing constructed from thermal insulating material. A front lens group and rear lens group are mounted within the housing adjacent opposite ends. The front and rear lens groups are thermally isolated from one another through the provision of two spaced windows therebetween that extend across and seal a light pathway running through the tubular housing. Preferably, the windows are sealingly mounted within the housing so as to define a vacuum chamber therebetween within the wall of the housing.

19 Claims, 3 Drawing Sheets

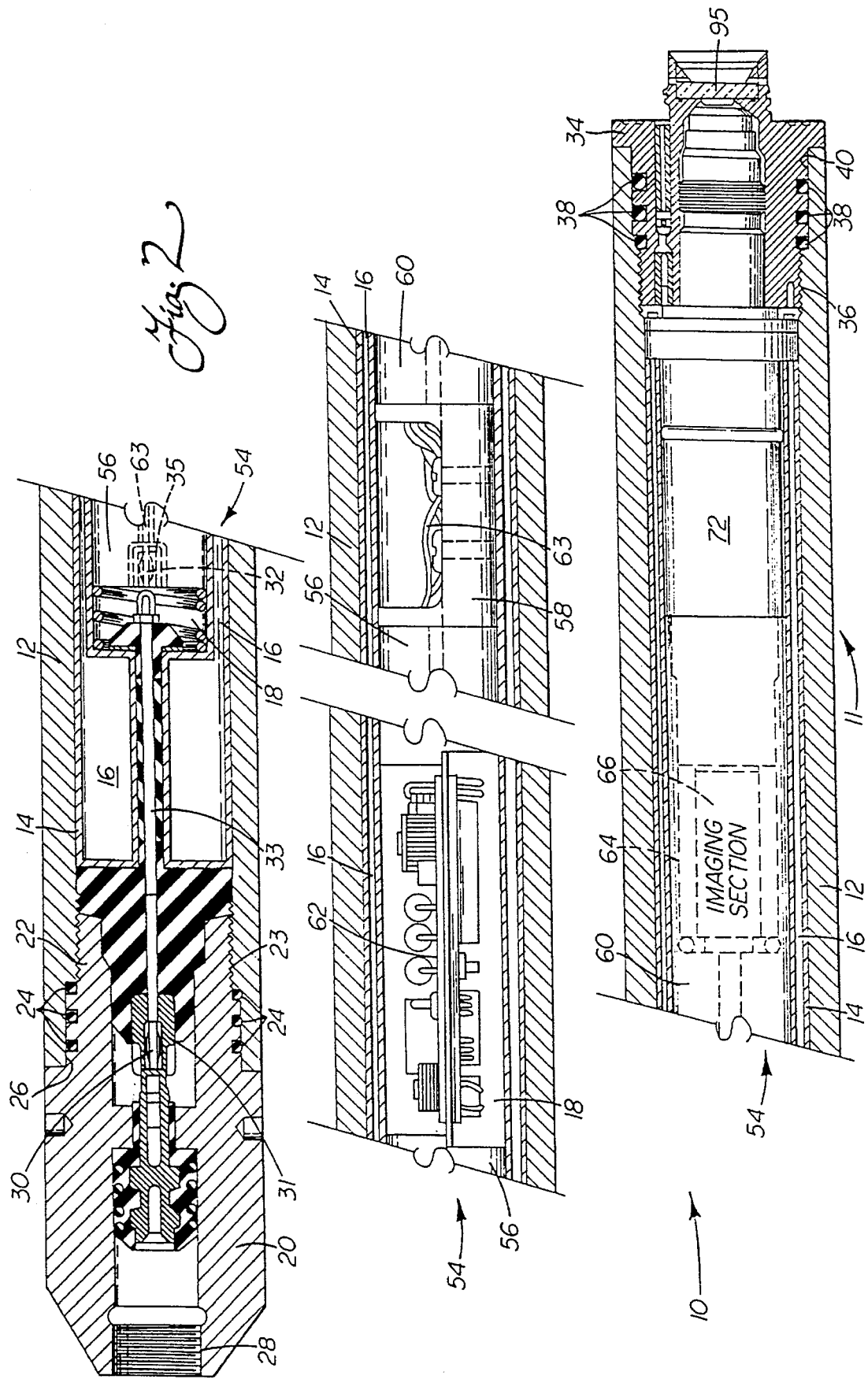

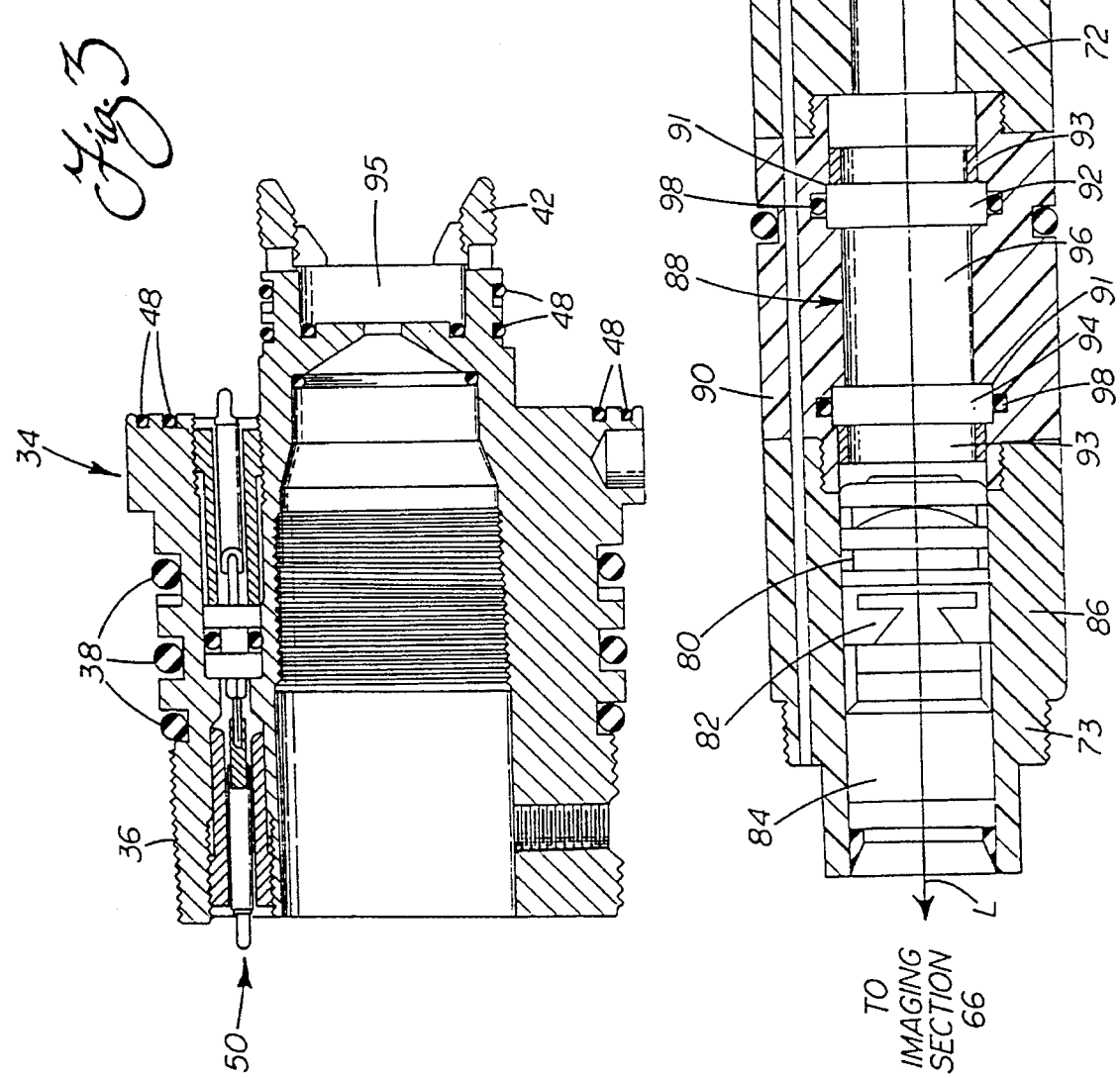

OPTIC SYSTEM FOR A DOWN HOLE CAMERA ASSEMBLY

This is a continuation-in-part application of our prior U.S. application Ser. No. 648,551, filed Jan. 31, 1991, abandoned, entitled "Down Hole Camera Assembly for Viewing a Bore Hole" and assigned to the assignee of the present invention.

TECHNICAL FIELD

The present invention relates generally to optic systems for cameras and, more particularly, to an optic system with improved thermal isolation from the operating environment such as may be utilized in a down hole camera assembly for logging bore holes.

BACKGROUND OF THE INVENTION

A bore hole or well bore is an artificially prepared hole, typically drilled into the ground with heavy duty drilling equipment in order to tap and extract underground water, oil, gas and other resources. Exploratory holes may also be drilled to locate mineral deposits, ground water, geothermal supplies and even to determine pollution levels at various depths in the ground.

It has long been known in the art that the visual examination of the strata forming the walls of a bore hole may be of significant value to a trained geologist. Such a visual examination may also be valuable in maintaining and repairing an operational bore hole. For example, after a steel casing has been in place in a bore hole for some time, rusting damage or shifts in the earth may cause rupturing or uncoupling of the steel casing. In such an instance, a visual examination of the casing shows the extent of the damage as well as the feasibility of repairs.

Further, in certain instances equipment may become lodged or stuck in the bore hole. This may result, for example, from either cave-ins or sedimentation during operation of the equipment. In such an instance, a camera may be lowered into the bore hole to locate the point of the cave-in and/or the lodged equipment and thereby determine the feasibility and approach for a recovery operation.

In order to achieve this end, a number of down hole camera apparatus, including video camera apparatus, have been developed. An example of one such apparatus is disclosed in U.S. Pat. No. 4,855,020 to Barbour. The Barbour patent discloses a down hole video camera apparatus wherein the video camera is held in the first section of a protective tubular housing. The video camera is equipped with a wide-angle lens to allow viewing of the wall of the bore hole. A lighthead assembly including a light source is attached to the housing. This light source illuminates the wall of the bore hole so as to allow videotaping in the bore hole as the camera assembly is lowered downwardly by means of a cable.

While down hole camera apparatus of the type disclosed in Barbour provide effective visual logging of bore holes, such prior art camera apparatus suffer a number of drawbacks that limit their application and usefulness. More particularly, such prior art camera apparatus incorporate conventional optic systems. These fail to provide sufficient thermal protection to the imaging section of the camera. In fact, the design of many prior art optic systems actually serves to direct or funnel the heat from the environment to the imaging section.

As temperatures of well over 300° F. are often encountered in deep bore holes, heat is quickly transferred. The resulting increase in temperature eventually reaches a level which causes the imaging section to cease operating. Hence, prior art down hole camera apparatus provide effective operation for only a limited period of time. In many instances the operational period is not sufficiently long to allow completion of the task at hand such as the viewing of a fishing operation. Accordingly, the camera must be brought up from the bore hole and cooled to an operating temperature or replaced with another camera before work may be completed. This is a time consuming and, therefore, expensive operation. Thus, a need is identified for a solution to this problem.

SUMMARY OF THE INVENTION

Accordingly, it is a primary object of the present invention to provide an optic system overcoming the above-described limitations and disadvantages of the prior art.

Another object of the present invention is to provide an optic system particularly adapted for use in a down hole camera assembly that is of relatively simple construction and that may be quickly serviced and more easily and economically maintained to provide peak operating performance.

Yet another object of the present invention is to provide an optic system furnishing significantly improved thermal isolation of the imaging section of the associated camera from the operating environment. Advantageously, this allows the imaging section to maintain a cooler operating temperature for a longer period of time. As a result, video images may be transmitted to the surface for significantly longer periods. In many instances, the added time allows completion of fishing operations, production and/or casing inspections with one camera in one down hole operation without costly delays.

A more specific object of the present invention is to provide an optic system for a down hole camera assembly that is specially adapted to allow down hole continuous camera operation in temperatures of up to 300° F. or more for up to three hours. Intermittent camera operation is possible at even higher temperatures such as 500° F. and at pressures of up to 15,000 psi.

Still another object of the present invention is to provide an optic system constructed from low thermal conductive materials wherein the front of the optic system is thermally isolated from the rear of the optic system so as to reduce the transfer of heat from the bore hole environment to the camera electronics.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an optic system is provided with improved thermal isolation properties that allow camera operation for longer periods of time in harsh operating environments. The optic system includes an elongated tubular housing constructed of thermal insulating material. Preferably the material has a thermal conductivity of at least as low as 1.5 W/m-C. Appropriate materials utilized for the construction of the housing include various resins including ULTEM and SUPEC resin both available from General Electric Company and PEEK resin available from TCI Corporation.

A light pathway is defined along the longitudinal axis of the housing. Front and rear lens groups are also provided in the light pathway. The front lens group is mounted adjacent a first or front end of the housing and the rear lens group is mounted adjacent a second or rear end of the housing. Further, means are provided for thermally isolating the front lens group from the rear lens group.

More particularly, the thermal isolation is provided by a pair of windows that are mounted so as to extend fully across the light pathway between the front and rear lens groups. The windows may be formed of quartz or optically pure glass that does not interfere with the optic system of the camera.

In the most preferred embodiment, the two windows are spaced from one another along the longitudinal axis of the housing while still being positioned between the front and rear lens groups. The windows are firmly mounted in position within the housing with an airtight seal about the periphery provided by O-rings or other means. Accordingly, it should be appreciated that a chamber is effectively defined between the windows and the wall of the tubular housing. A vacuum may be drawn on this chamber to provide a negative pressure thermal buffering zone that significantly reduces the transfer of heat through the optic lens system from the front of the optic system, located adjacent the environment, to the rear of the optic system, located adjacent the temperature sensitive imaging section of the camera electronics.

As the present invention significantly reduces the transfer of heat, the camera electronics may now function for an additional length of time even in the harsh, high temperature operating environment of a bore hole. In fact, depending upon the type of housing in which the camera and optic system of the present invention are maintained, the additional operation time may be extended as much as two times or more than possible for the same housing and camera section when equipped with a conventional optic system. Such additional time often allows an inspection to be completed in one down hole operation. This represents a significant advantage as prior art systems often meet with costly delays necessary to cool a camera or lower a second camera into the bore hole after the first ceases operation.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing:

FIG. 2 is a cross-sectional view of the down hole camera assembly equipped with the present optic system;

FIG. 3 is a detailed cross-sectional view of the front subassembly of the camera assembly; and FIG. 4 is a detailed cross-sectional view of the optic system of the present invention.

Figure 1:
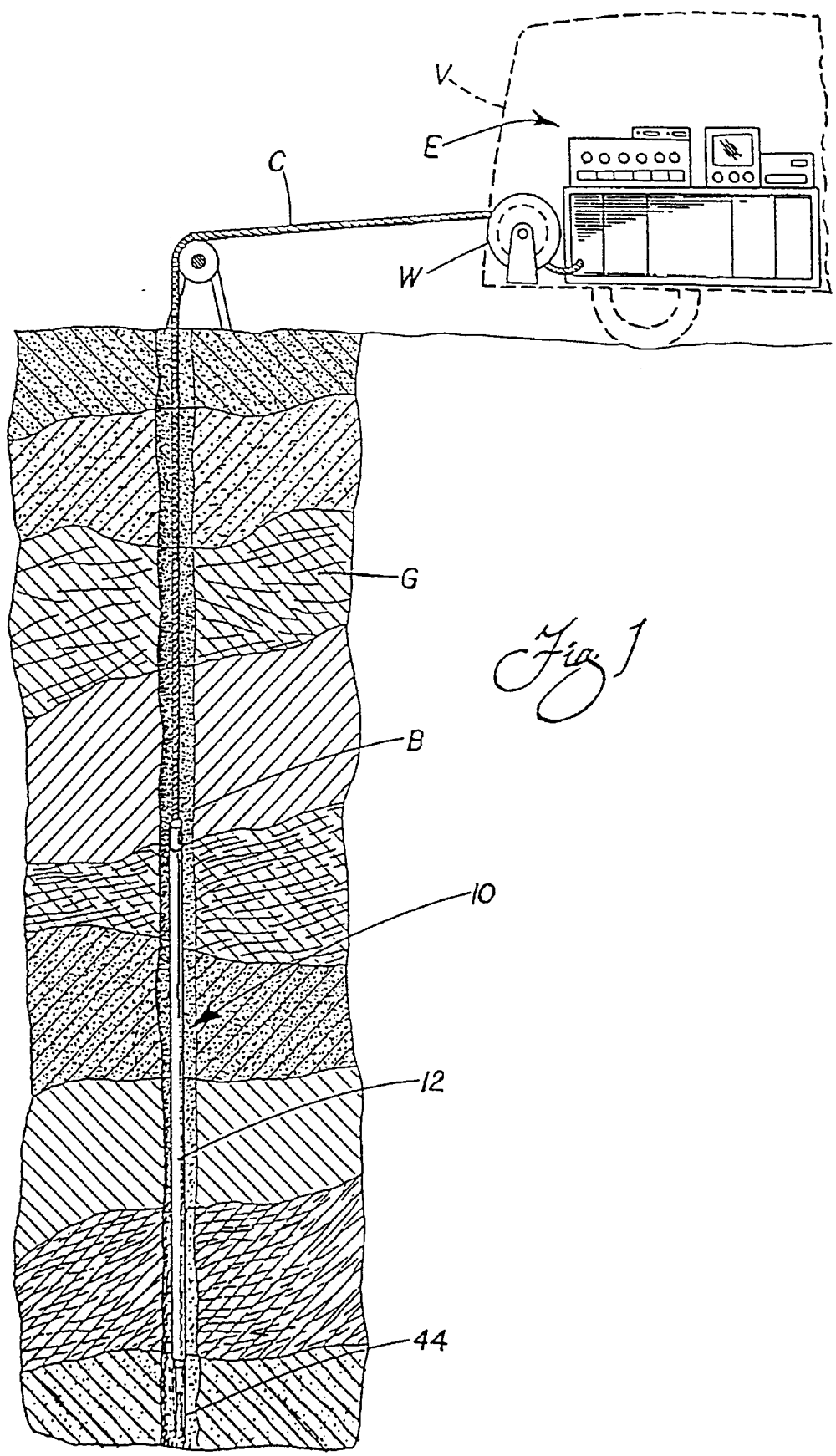
FIG. 1 is a schematical representation of a down hole camera assembly incorporating the optic system of the present invention as the assembly is being lowered into a bore hole by means of a cable being payed out by a winch in an equipment van.

Reference will now be made in detail to the present preferred embodiment of the invention, an example of which is illustrated in the accompanying drawing.

DETAILED DESCRIPTION OF THE INVENTION

Reference is now made to the drawing figures and particularly FIGS. 1 and 2 showing a down hole camera assembly 10 in which is incorporated the optic system 11 of the present invention. The camera assembly 10 being described is the subject of our copending patent application Ser. No. 648,551, entitled "Down Hole Camera Assembly for Viewing a Bore Hole", filed Jan. 31, 1991, and assigned to the assignee of the present invention. The complete disclosure of this application is incorporated herein by reference. Of course, it should be appreciated that the optic system 11 of the present invention may be utilized with other camera assemblies as desired and that this complete description is only being presented for purposes of illustration.

As shown in FIG. 1, the down hole camera assembly 10 is being lowered into a bore hole B extending downwardly into the ground. This lowering is accomplished by means of cable C being payed out by a winch W from an equipment van V. The equipment van V houses a video display monitor, video printer, video cassette recorder and other appropriate control components, generally designated by reference letter E, as are known in the video logging art. The bore hole B being visually monitored may be any hole previously drilled for any appropriate purpose including exploration and resource tapping/recovery.

As best shown in FIG. 2, the camera assembly 10 includes an outer housing 12. Preferably, the outer housing 12 is formed from high strength tubular steel capable of withstanding pressures of 17,000 psi or more. An inner housing 14 is concentrically received within the outer housing 12. The inner housing 14 is protected from direct contact with the wall of the bore hole B and hence impact damage by the hard outer housing 12. Of course, the outer housing 12 also serves to isolated the inner housing 14 from the high temperature environment generally found in bore holes. The inner housing 14 is specially designed to further thermally isolate the camera components from those high temperatures that may exceed 500° F. in particular bore holes and at particular depths in various places of the world.

More particularly, the inner housing 14 includes a sealed evacuated space 16 that extends around the entire circumference of the housing. This vacuum space 16 provides significant thermal isolation so as to maintain temperatures in the chamber 18 within the inner housing 14 relatively cool compared to the bore hole environment. These cooler temperatures allow the camera components to operate in a reliable manner for longer periods of time underground. Such an inner housing 14 or vacuum flask may be obtained from Vacuum Barrier Corporation.

A rear subassembly 20 seals the rear end of the outer housing 12. More particularly, the rear subassembly includes a projection 22 having threads 23 that engage cooperating threads in the outer housing 12. Three O-ring seals 24 carried in grooves on the projection 22 engage and seal against a counter bore 26 formed in the outer housing 12.

The rear subassembly 20 also includes a cable head 28 adapted to receive and hold the distal end of the cable C upon which the camera assembly 10 is lowered into and raised from the bore hole B. All control lines including power and video from the equipment E in the van V run through the cable C and are connected to the banana plug connector 30 in the rear subassembly 20. A cooperating female connector 31 mounted on the rear of the inner housing 14 mates with the banana plug connector 30. The connector 31 is operatively connected to a second banana plug connector 32 on the inner housing 14 by means of an electrical conductor (not shown) that extends through the centrally disposed and electrically insulated bore 33. This connector 32 mates with a cooperating female connector 35 mounted in the rear of the camera chassis 54 that is described in greater detail below. In this way, operative connection to the various camera components is provided.

A front subassembly 34 seals the front of the outer housing 12. More specifically, as shown in detail in FIG. 3, the front subassembly 34 includes a series of threads 36 that mate with cooperating threads machined in the outer housing 12 (note also FIG. 2). Three O-ring seals 38 received in grooves in the front subassembly 34 engage and seat against the walls of a counter bore 40 formed in the distal end of the outer housing 12.

The front subassembly 34 also includes a second set of threads 42 for engaging a cooperating set of threads of a lighthead assembly 44 of a type known in the art (see FIG. 1). The O-ring seals 48 provided in grooves of the front subassembly 34 engage and firmly seal against surfaces of the lighthead assembly 44. An electrical feed, generally designated by reference numeral 50, in the front subassembly 34 feeds electrical power to the light head assembly 44. The light head assembly 44 serves to illuminate the bore hole B to allow visual logging.

A substantially rigid camera chassis 54 is received and held in the chamber 18 within the inner housing 14. The camera chassis 54 includes a first heat sink 56 connected by means of a coupling 58 to a second heat sink 60. Preferably, the heat sinks 56, 60 are formed from brass or other appropriate heat absorbing material. The coupling 58 is formed from a thermal insulating material such as a polyetherimide resin. One appropriate material that may be utilized for the coupling 58 is ULTEM resin.

The first heat sink 58 includes an intermediate plate-like portion to which the power/transmission section 62 of the camera is mounted. Heat produced by the power/transmission section 62 during operation of the camera is absorbed by the heat sink 56 and thereby drawn away from the power/transmission section so as to allow cooler, more reliable operation. An appropriate power/transmission section 62 for the camera may be obtained from Laval Underground Surveys.

Heat sink 60 includes a cavity 64 at its forward end adapted to receive and hold the imaging section 66 of the camera. The imaging section 66 may, for example, be obtained from a Pulnix 6x–7x camera. The heat sink 60 serves to absorb heat generated by the imaging section 66 during operation of the camera thereby also maintaining the imaging section at a lower temperature for more reliable operation.

Advantageously, it should be appreciated that the thermally insulated coupling 58 substantially prevents the transfer of heat from the heat sink 56 to the heat sink 60. This is important as the power/transmission section 62 of the camera generates more heat and is also able to operate at higher temperatures than the imaging section 66. Further, it should be appreciated that by adjusting the relative lengths and mass of the heat sinks 56, 60, heat absorption may be tuned to meet the particular operating characteristics of the camera components being utilized to provide the best and most reliable camera function. It is the imaging section 66 that is operatively held adjacent and immediately behind the optic system 11 of the present invention.

More specifically, the optic system 11 includes an elongated tubular housing 72 that may be rigidly mounted to the camera chassis 54 by mating threads 73 formed at the rear of the housing and on the inner wall of the cavity 64 in the heat sink 60. The elongated housing 72 of the system 11 is formed from thermally insulating material. This material has a thermal conductivity of at least as low as 1.5 W/m-C. Materials providing this level of thermal conductivity include polyetherimide resins such as ULTEM resin. Examples of other materials that may be utilized include resins sold under the trademarks PEEK and SUPEC.

As shown in FIG. 4, the tubular housing 72 may be formed from three sections that are joined together by means of cooperating threads. This modular construction simplifies repair and maintenance operations. A front lens group 74 of a pin hole lens such as a 5.5 mm Rainbow pin hole lens is mounted in the front section 76 of the housing 72. A 60° fixed view lens 78 is provided at the front of the front section of the pin hole lens 74. A middle lens group 80, iris 82 (for example F 8.0) and rear lens group 84 are also mounted and held in a rear section 86 of the housing 72. The various lens groups may be securely held within the housing 72 by any appropriate means known in the art.

The front section 76 and front lens group 74 are thermally isolated from the rear section 86 and rear lens group 84 by a thermal isolation assembly generally designated by reference number 88 that is contained within the middle section 90 of the housing 72. More particularly, the assembly 88 includes a first window 92 mounted toward the front end of the middle section 90. A second window 94 is mounted near a rear end of the middle section 90. Again, any known method of mounting may be utilized. For purposes of illustration, the windows 92, 94 are shown mounted within the tubular housing 72 through the provision of cooperating mounting shoulders 91 in the middle housing section 90 and threaded retaining rings 93.

The windows 92, 94 extend fully across the longitudinally extending light pathway L defined by the hollow section of the tubular housing 72. The windows 92, 94 may be formed from optically pure glass or quartz. Such material allows the recording of clear images by the imaging section 66 of the camera while also providing good thermal insulation properties resisting the transfer of heat from the front of the optic system located directly behind the viewing window 95 (see FIGS. 2 and 3) to the rear of the optic system located adjacent the imaging section 66 of the camera.

Where further thermal insulation is desired as necessary for extended operation of a down hole camera in certain high temperature bore holes B, a sealed chamber 96 may be formed between the windows 92, 94 and the wall of the middle housing section 90. For example, sealing between the windows 92, 94 and the middle housing section 90 may be provided by means of one or more O-ring seals 98.

A vacuum may be drawn on the chamber 96 so as to form a negative pressure zone that is particularly effective in slowing the transfer of heat through the optic system 11 toward the imaging section 66 of the camera. As the optic system has been the primary heat transfer pathway between the environment and the camera electronics in prior art down hole camera designs, the present optic system 11 with significantly enhanced thermal isolation represents a significant advance in the art. The resulting more reliable and dependable camera performance over extended periods of time even during continuous operation significantly reduce overall costs and the time necessary in completing various down hole inspections.

In summary, numerous benefits result from employing the concepts of the present invention. Advantageously, a camera assembly 10 equipped with the specially designed optic system 11 of the present invention remains significantly cooler even in the harshest operating environments as a result of the thermal insulation provided by the windows 92, 94 and vacuum chamber 96 contained in the middle housing section 90. This thermal protection allows the camera to operate for extended periods in time in environmental conditions where such operation would be impossible with prior art designs. This is clearly a significant advantage particularly when one considers the time necessary to inspect bore holes ranging down to 20,000 feet or more in depth.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

We claim:

1. An optic system for a down hole camera, comprising:
    an elongated tubular housing constructed of thermal insulating material defining a light pathway;
    a front lens;
    a rear lens;
    means for mounting said front lens adjacent a first end of said housing and said rear lens adjacent a second end of said housing, both of said lenses being mounted in said light pathway; and
    means for thermally isolating said front lens from said rear lens being characterized by;
    a vacuum chamber formed in said tubular housing along said light pathway.

2. The optic system set forth in claim 1, wherein said thermally isolating means includes a first window mounted across said light pathway between said first and second lenses.

3. The optic system set forth in claim 2, wherein said thermally isolating means includes a second window spaced from said first window and mounted across said light pathway between said first and second lenses.

4. The optic system set forth in claim 3, including means for sealingly mounting said first and second windows in said housing.

5. The optic system set forth in claim 4, wherein said first and second windows are formed from quartz.

6. The optic system set forth in claim 4, wherein said first and second windows are formed from glass.

7. The optic system set forth in claim 4, wherein said vacuum chamber is formed between said first and second windows and said tubular housing.

8. The optic system set forth in claim 1, wherein said thermally insulating material has a thermal conductivity of at least as low as 1.5 W/m-C.

9. The optic system set forth in claim 1, wherein said elongated tubular housing includes front, rear and middle sections that are joined together.

10. The optic system set forth in claim 9 wherein said thermally isolating means includes a first window mounted across said light pathway between said first and second lenses.

11. The optic system set forth in claim 10, wherein said thermally isolating means includes a second window spaced from said first window and mounted across said light pathway between said first and second lenses.

12. The optic system set forth in claim 11, including means for sealingly mounting said first and second windows in said housing.

13. The optic system set forth in claim 12, wherein said first and second windows are formed from quartz.

14. The optic system set forth in claim 12, wherein said first and second windows are formed from glass.

15. The optic system set forth in claim 14, wherein said vacuum chamber is formed between said first and second windows and said tubular housing.

16. The optic system set forth in claim 15, wherein said thermally insulating material has a thermal conductivity of at least as low as 1.5 W/m-C.

17. The optic system set forth in claim 16, wherein said front lens is mounted in said front section of said housing, said rear lens is mounted in said rear section of said housing and said first and second windows are mounted in said middle section of said housing.

18. An optic system for a down hole camera, comprising:
    an elongated tubular housing constructed of thermally insulating material defining a light pathway;
    lens means held in said housing to focus light for imaging;
    means for mounting said lens means in said housing; and
    means for thermally isolating said optic system from said camera characterized by:
    a first window mounted in said housing sealing across said light pathway, a second window mounted in said housing sealing across said light pathway and spaced from said first window, and a vacuum chamber formed between said first and second windows and said tubular housing.

19. The optic system set forth in claim 18, wherein said thermally insulating material has a thermal conductivity of at least as low as 1.5 W/m-C.

* * * * *